US012751786B2

(12) United States Patent
Hengerer et al.

(10) Patent No.: US 12,751,786 B2
(45) Date of Patent: Oct. 6, 2026

(54) DRAPING A WALL OF AN IMAGING DEVICE

(71) Applicants: Siemens Healthcare GmbH, Erlangen (DE); The Regents of the University of Michigan, Ann Arbor, MI (US)

(72) Inventors: Arne Hengerer, Möhrendorf (DE); Vikas Gulani, Ann Arbor, MI (US)

(73) Assignees: Siemens Healthineers AG, Forchheim (DE); The Regents of the University of Michigan, Ann Arbor, MI (US)

( * ) Notice: Subject to any disclaimer, the term of this patent is extended or adjusted under 35 U.S.C. 154(b) by 459 days.

(21) Appl. No.: 18/230,857

(22) Filed: Aug. 7, 2023

(65) Prior Publication Data

US 2024/0065791 A1 Feb. 29, 2024

(30) Foreign Application Priority Data

Aug. 23, 2022 (EP) .................................... 22191668

(51) Int. Cl.
*A61B 46/10* (2016.01)
*A61B 5/055* (2006.01)

(52) U.S. Cl.
CPC .............. *A61B 46/10* (2016.02); *A61B 5/055* (2013.01)

(58) Field of Classification Search
CPC ............ A61B 2503/04; A61B 2503/06; A61B 2046/205; A61B 2050/002; A61M 2029/025
USPC ...................... 128/849, 851, 855, 856; 378/4
See application file for complete search history.

(56) References Cited

U.S. PATENT DOCUMENTS

| | | | | |
|---|---|---|---|---|
| 2003/0181810 | A1* | 9/2003 | Murphy | A61L 31/18 600/427 |
| 2008/0216844 | A1* | 9/2008 | Olfert | A61B 6/4423 128/856 |
| 2015/0114404 | A1 | 4/2015 | Czop et al. | |
| 2016/0074268 | A1* | 3/2016 | Breegi | A61G 11/009 600/21 |
| 2020/0054299 | A1 | 2/2020 | Daley, II et al. | |

FOREIGN PATENT DOCUMENTS

| | | | | |
|---|---|---|---|---|
| DE | 102004007427 | A1 | 9/2005 | |
| DE | 102010040956 | A1 * | 3/2012 | A61B 46/10 |
| WO | WO-9816167 | A1 * | 4/1998 | A61B 46/00 |

OTHER PUBLICATIONS

DE 102010040956 machine translation (Year: 2012).*

* cited by examiner

*Primary Examiner* — Caitlin A Carreiro
(74) *Attorney, Agent, or Firm* — Lempia Summerfield Katz LLC

(57) ABSTRACT

Image guided interventions are performed in a sterile environment. A device is provided for imaging at least a part of a patient, wherein the device includes a detection apparatus having a tunnel through which or into which the patient is configured to be transported for imaging purposes. A sterile cover rolled up or folded is provided at the outside of the tunnel. A covering mechanism is capable of unrolling or unfolding the sterile cover and draping the sterile cover in the tunnel, such that the inner wall of tunnel is at least partially covered by the sterile cover.

8 Claims, 3 Drawing Sheets

DRAPING A WALL OF AN IMAGING DEVICE

The present patent document claims the benefit of European Patent Application No. 22191668.7, filed Aug. 23, 2022, which is hereby incorporated by reference in its entirety.

TECHNICAL FIELD

The present disclosure relates to a device for imaging at least a part of a patient including a detection apparatus, which includes a tunnel (also called bore) through which or into which the patient may be transported for imaging purposes. Furthermore, the present disclosure relates to a method of covering or draping a tunnel of the mentioned device.

BACKGROUND

In minimally invasive medical procedures, medical instruments, such as catheters and/or single-use needles, are inserted into a patient, e.g., with image monitoring of the procedure. Image monitoring allows the acquisition of images in which the medical instrument is visualized in relation to its anatomical surroundings. While X-ray imaging has been used for image monitoring of minimally invasive medical procedures, particularly fluoroscopy, it has now also been proposed to use magnetic resonance devices, hence magnetic resonance (MR) imaging, for image monitoring. This may be referred to as interventional MR imaging. When using so-called closed magnetic resonance devices, which have a main magnet with a cylindrical patient receiving area in which the homogeneity volume is located, it is necessary to work in a confined space, which may be sterile for the intervention.

A special type of medical instruments used for minimally invasive medical procedures may be interventional needles, which may be used for biopsy, ablation, or brachytherapy. It has also been proposed to propagate needles under real-time magnetic resonance control.

It is a common challenge to maintain a sterile field when performing image-guided intervention in both CT (computer tomography) and MRT (magnetic resonance tomography) and any other potential setting with a bore or tunnel through which the patients are put into or pulled out before and after the procedure. In such procedures, needles, biopsy guns, introducers, wires, or other devices are partially in the patient and partially outside of the patient. Other materials such as unsterile towels or drapes may be resting on the patient. When the patient is moved into or out from the imaging device (e.g., scanner) on a moving table, there is a risk that these unsterile materials contact the device bore, thereby breaking sterility. This may result in the need to dispose of the equipment, repeat parts of the procedure or, in the worst case, abort the procedure.

SUMMARY AND DESCRIPTION

Thus, the object of the present disclosure is to provide a device for imaging at least a part of a patient which reduces the risk of breaking sterility.

This object is solved by the devices and methods described herein. The scope of the present disclosure is defined solely by the appended claims and is not affected to any degree by the statements within this summary. The present embodiments may obviate one or more of the drawbacks or limitations in the related art.

Accordingly, there is provided a device for imaging at least a part of a patient including a detection apparatus including a tunnel configured to receive the patient, i.e., through which or into which the patient may be transported for imaging purposes. For instance, such device is a CT or MRT equipment configured to perform an image guided intervention. Such a CT or MRT device may have a tunnel or bore for the patient to be screened. The patient may be placed on a patient table that may be moved forward and backward along the table's longitudinal axis. This patient table allows the patient to be pushed or automatically moved into the tunnel of the imaging device. The tunnel represents an examination area in which the patient or a part of the patient may be screened.

The device includes a sterile cover rolled up or folded at the outside of the tunnel. The sterile cover may be provided directly on the outside of the tunnel. The sterile cover may be made of any kind of foil, fabric, film, or tissue that is sterile itself. A paper or a plastic film may form this cover, being rolled up or folded before use. For example, the cover is rolled up on a stick or a paper roll. Alternatively, the cover is exactly folded or just unsystematically compressed at the outside of the tunnel. Because the cover is provided at the outside of the tunnel, the cover may be applied easily in the tunnel by pulling the cover through the tunnel. The device is not limited to one single sterile cover being provided at the outside of the tunnel. A plurality of sterile covers may be provided there in a rolled up or folded state.

The device is provided with a covering mechanism capable of unrolling or unfolding the sterile cover and draping it in the tunnel, such that the inner wall of the tunnel is at least partly covered by the sterile cover. This means that the covering mechanism may pick up the film or cover on one side of the tunnel and pull it through the tunnel. Other techniques of draping the tunnel are described below.

The goal is to provide a sterile environment for each image guided intervention. Thus, it is helpful to cover at least a part of the tunnel or to cover at least the intervention area so that a part of the tunnel or the complete tunnel is protected.

In an embodiment of the device, the detection apparatus is based on MRT technology or CT technology. As indicated above, these technologies may include imaging sections having a tunnel or bore that has to be covered by the sterile cover. Additionally, these technologies may be used for performing image guided interventions.

A further embodiment of the device includes a table for transporting the patient into the tunnel, wherein the table may be moved into the tunnel being covered by the sterile cover without damaging the sterile cover. During transport into the screening area, (e.g., the bore or tunnel), of the scanner, the patient may lie on the table. The table may be moved automatically into the tunnel. Thus, the table being moved shall not damage or destroy the sterile cover. This may require that the table is not supported in the tunnel. The table has to be supported outside the tunnel whereby the table forms a kind of cantilever. This cantilever may be moved linearly into the tunnel and out of it.

According to a further embodiment, the sterile cover has a cylindrical or tube shape with a diameter of the order of the tunnel. For example, the sterile cover is a plastic film tube. The tube may have a diameter that is the same or similar to the diameter of the inner wall of the tunnel. Thus, the already small diameter of the tunnel is not lowered by the tube shaped cover.

Furthermore, the sterile cover may be one of a series of covers each separated from the other by a respective perforation. In this case, a plurality of covers is fixed together in order to form a structure of a large number of covers. This structure may also be folded or rolled up at the outside of the tunnel. The covering mechanism may be able to separate one cover from the structure of covers by cutting the perforation. Alternatively, the perforation may be cut by a user and the covering mechanism just drapes the separated cover in the tunnel.

Moreover, the covering mechanism may include umbrella device for unfolding the sterile cover and for pressing the sterile cover to the inner wall of the tunnel when the umbrella device is pushed through the sterile cover in the tunnel. For instance, when the cover has a tube shape in the unfolded state, the cover may be flat when folded. In order to unfold such flat cover, it may be necessary to press the cover from the inside out. Such radial pressing may be performed by the umbrella device. The tip of the umbrella device opens the folded cover and the distal ends of the umbrella device press the cover towards the inner wall of the tunnel.

Alternatively, the sterile cover may be a single-layer film rolled up on a roll, wherein the covering mechanism includes a guiding element that is capable of guiding the roll in the tunnel in a circumferential direction along the inner wall, thereby unrolling the sterile cover. This means, that the sterile cover is rolled up on a roll, which may be provided outside the tunnel before starting the draping of the tunnel. In one act of draping, the covering mechanism may transport the roll into the tunnel, thereby aligning the rotation axis of the roll in parallel to the center axis of the tunnel. In an additional act, the covering mechanism or a user may fix the one end of the sterile cover at the inner wall of the tunnel. Afterwards, the covering mechanism may drive the roll along the inner circumference of the tunnel. Thereby, the sterile cover on the roll is unrolled.

According to another embodiment, the sterile cover is fixed in a rolled up state or a folded state at a first axial end of the tunnel, and the covering mechanism includes a guiding element that is capable of automatically pulling the sterile cover through the tunnel in its axial direction to a second axial end of the tunnel opposite to the first axial end, thereby unrolling or unfolding the sterile cover. For instance, the sterile cover may be pulled through the tunnel like a curtain with two panels, so that the cover is draped like a tent in the tunnel. The covering mechanism may include more than one guiding element so that the cover has a respective polygon shape within the tunnel. Thereby, each guiding element may be provided with a hook, a clamp, or the like for fixing the cover for pulling it through the tunnel.

The sterile cover and/or the inner wall of the tunnel may include sticky material to fix the sterile cover at the inner wall of the tunnel. The sticky material may include glue or a Velcro® fastener or the like. The sticky material guarantees that the cover remains fastened at the inner wall of the tunnel during the intervention. The glue or adhesive may be completely removed from the inner wall when the sterile cover originally provided with the glue is detached from the inner wall. Otherwise, when the sticky material is provided originally at the inner wall, detachment of the sterile cover may not lead to a tearing of the cover.

As already indicated above, the sterile cover may be made of paper or a plastic film. Such paper or plastic film are cheap materials predestinated for single use. The paper may be made of multi-layer material. Furthermore, the material of the sterile cover may be a composite material including paper and a plastic film. Moreover, the paper may also be laminated or sprayed with plastic.

A system is also provided for performing an image guided intervention, wherein the system includes a device for imaging as described above and an intervention device. The intervention device may be an ablation needle, a biopsy gun, an introducer, a guiding wire, or the like. Each of these intervention devices will be contaminated when used for the intervention. The intervention device may touch the inner wall of the tunnel of the imaging device so that sterility is broken. For avoiding such situation, the tunnel of the imaging device or the intervention device itself is covered by the sterile cover.

Furthermore, a method is provided for covering a tunnel of a device, wherein the covering mechanism includes umbrella device for unfolding the sterile cover and for pressing the sterile cover to the inner wall of the tunnel then the umbrella device is pushed through the sterile cover in the tunnel. The method includes providing the sterile cover having a cylindrical shape at a first axial end of the tunnel and both unfolding and pressing the sterile cover to the inner wall of the tunnel by pushing the umbrella device through the sterile cover in the tunnel. The method may be complimented and varied according to the above-described device.

Alternatively, a method of covering a tunnel of a device as mentioned above is provided, wherein the sterile cover is a single-layer film rolled on a roll and the covering mechanism includes a guiding element that is capable of guiding the roll in the tunnel in the circumferential direction along the inner wall, thereby unrolling the sterile cover. The method includes providing the sterile cover as a single-layer film rolled up on the roll, wherein an axis of the roll is aligned in parallel to the center axis of the tunnel and guiding the roll in the tunnel in the circumferential direction along the inner wall, thereby keeping the axis of the roll in parallel to the center axis of the tunnel and unrolling the sterile cover. This method may be complemented and varied according to the corresponding device mentioned above.

Furthermore, there is provided a method of covering a tunnel of a device as mentioned above, wherein the sterile cover is fixed in a rolled up state or a folded state at a first axial end of the tunnel, and the covering mechanism includes a guiding element that is capable of automatically pulling the sterile cover through the tunnel in its axial direction to a second end of the tunnel opposite to the first end, thereby unrolling or unfolding the sterile cover. The method includes providing the sterile cover in a rolled up state or a folded state at the first axial end of the tunnel, and automatically pulling the sterile cover through the tunnel in an axial direction to the second end of the tunnel opposite to the first end by a (linear) guiding element, thereby unrolling or unfolding the sterile cover. This method also may be complimented and varied similar to the device mentioned above.

A computer program product is directly loadable in a memory unit of a programmable controller unit and has program code for executing a method as described herein, (e.g., automatically unfolding the sterile cover in the tunnel) when the computer program product is executed in the controller unit. This allows the method to be executed in a fast, identically repeatable, and robust manner. The computer program product is configured in such a way that it may execute the method acts by the control unit. The control unit has, in each case, the prerequisites, such as a corresponding working memory, a corresponding graphics card, or a corresponding logic unit, so that the respective process acts may be executed efficiently. The computer program product is stored, for example, on an electro-readable medium or deposited on a network or server, from where it may be loaded into the processor of a local control unit, which may be directly connected to the magnetic resonance device or designed as part of the magnetic resonance device. Furthermore, control information of the computer program product may be stored on an electronically readable data carrier. The control information of the electronically readable data carrier may be designed to perform a procedure when the data carrier is used in a control unit of a magnetic resonance apparatus. Examples of electronically readable data carriers are a DVD, a magnetic tape, or a USB stick on which electronically readable control information, in particular software, is stored. If this control information (software) is read from the data carrier and stored in a control unit of a magnetic resonance apparatus, all embodiments of the methods described above may be carried out.

The advantages of the magnetic resonance apparatus and the computer program product correspond to the advantages of the method, which are described in detail above. Features, advantages, or alternative embodiments mentioned herein may likewise be transferred to the other claimed objects and vice versa.

Further advantages, features, and details of the disclosure are apparent from the examples of embodiments described below and from the drawings.

For use cases or use situations that may arise in the method, and which are not explicitly described here, it may be provided that, in accordance with the method, an error message and/or a prompt for user feedback is output and/or a default setting and/or a predetermined initial state is set.

BRIEF DESCRIPTION OF THE DRAWINGS

The present disclosure is now described in more detail along with the following figures showing.

DETAILED DESCRIPTION

The following embodiments described in more detail represent non-limiting examples of the present disclosure.

Figure 1:
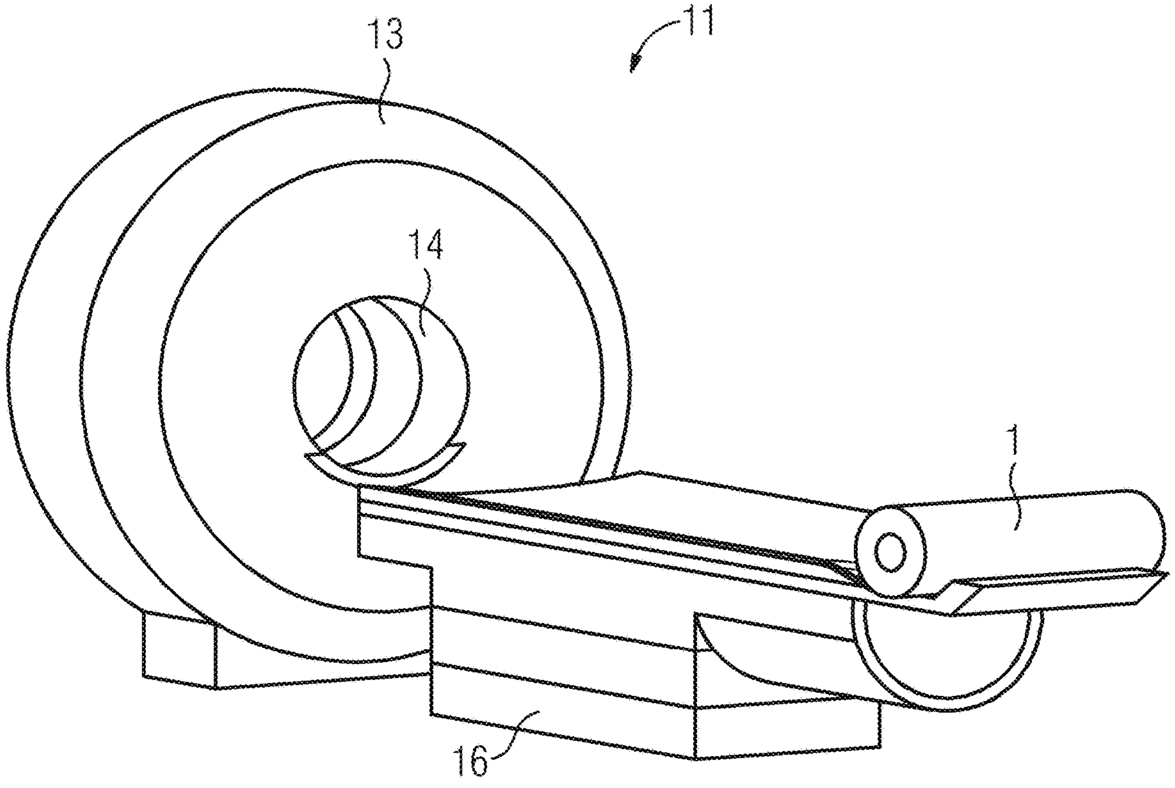
FIG 1 PRIOR ART
FIG. 1 depicts an MRT system according to the prior art.
Figure 2:
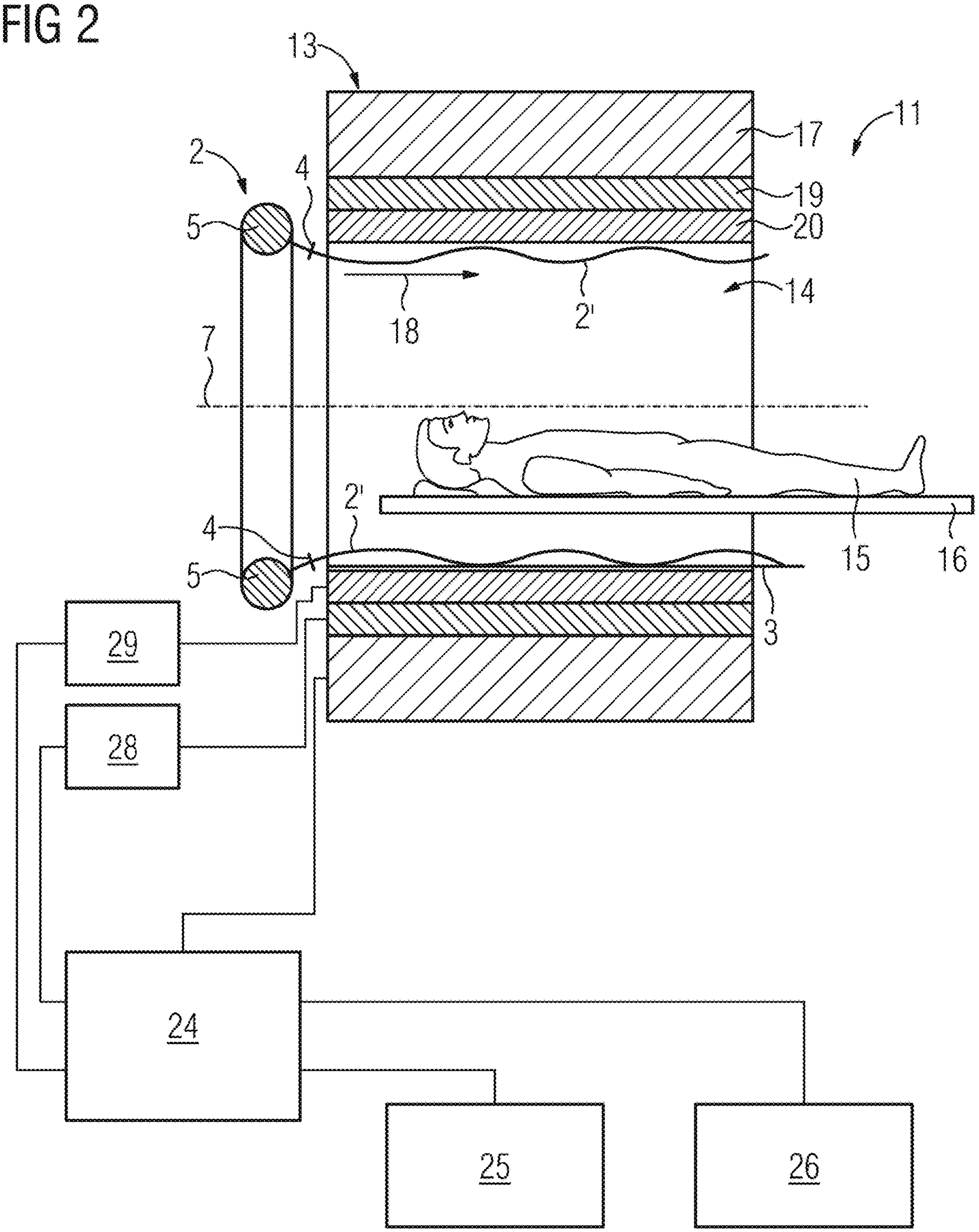
FIG. 2 depicts a sectional view of an example of a magnetic resonance device with controlling components as block diagram.

FIGS. 1 and 2 show a magnetic resonance device 11 (MRT device) as imaging device for performing an image guided intervention in a schematic representation.

The perspective view of FIG. 1 shows the magnetic resonance device 11 including the magnet unit 13 as a detection apparatus for gathering images of a patient or a part of a patient. For this purpose, the patient has to be introduced into a tunnel 14 of the magnet unit 13. A patient table 16 is provided in front of the magnet unit 13 on which the patient may lie down. The patient table 16 may be designed to position the patient in the tunnel 14 (semi-) automatically.

In order to guarantee sterility of the patient table 16, a paper roll 1 is provided at the foot of the patient table 16. The paper of the paper roll 1 may be pulled over the lying surface of the patient table 16.

As shown in FIG. 2, the magnetic resonance apparatus 11 includes a detection apparatus formed by the magnet unit 13 with a main magnet 17 for generating a strong and, in particular, constant main magnetic field 18. In addition, the magnetic resonance apparatus 11 has the cylindrical patient-receiving tunnel 14 for receiving a patient 15, the patient-receiving tunnel 14 being surrounded in a cylindrical manner in a circumferential direction by the magnet unit 13. The patient 15 may be pushed into the patient receiving tunnel 14 by the patient table 16 of the magnetic resonance apparatus 11.

The magnet unit 13 further includes a gradient coil unit 19 used for location coding during imaging. The gradient coil unit 19 is controlled by a gradient control unit 28. Further, the magnet unit 13 has a high-frequency antenna unit 20 and a high-frequency antenna control unit 29 for exciting a polarization established in the main magnetic field 18 generated by the main magnet 17. The high-frequency antenna unit 20 is controlled by the high-frequency antenna control unit 29 and irradiates high-frequency pulses into an examination space formed by the patient receiving tunnel 14.

For controlling the main magnet 17, the magnetic resonance apparatus 11 includes a control unit 24. The control unit 24 centrally controls the magnetic resonance apparatus 11, such as performing MR control sequences. The control unit 24, together with the magnetic unit 13, may be referred to as the recording unit or a detection apparatus. In addition, the control unit 24 includes an unspecified reconstruction unit for reconstructing medical image data acquired during the magnetic resonance examination. The magnetic resonance apparatus 11 includes a display unit 25. Control information, such as control parameters, as well as reconstructed image data may be displayed on the display unit 25, (e.g., on at least one monitor), for a user. In addition, the magnetic resonance apparatus 11 has an input unit 26 by which information and/or control parameters may be input by a user during a measurement process. The control unit 24 may include the gradient control unit 28 and/or the high-frequency antenna control unit 29 and/or the display unit 25 and/or the input unit 26.

The control unit 24 may include computer programs and/or software, which are directly loadable in an unspecified memory unit of the control unit 24 for controlling covering mechanism. For this purpose, the control unit 24 may include a processor, not shown in more detail, which is adapted to execute the computer programs and/or software. Alternatively, the computer programs and/or software may also be stored on an electronically readable data carrier formed separately from the control unit 24, whereby data access from the control unit 24 to the electronically readable data carrier may take place via a data network.

The magnetic resonance device 11 may include further components as well. Moreover, a general mode of operation of a magnetic resonance apparatus 11 is known to those skilled in the art, so that a detailed description of the further components is dispensed with.

During an intervention, the MRT device 11 may be contaminated by the patient, by the instruments used, by the physician and the like. The main idea of the present disclosure therefore is to avoid contamination by draping the bore or tunnel 14 of the imaging device. In FIG. 2, the principal device or system for realizing this draping of tunnel 14 are shown schematically. First of all, a sterile cover 2 is provided at the entrance of tunnel 14, e.g., outside of the tunnel 14. The sterile cover 2 is provided in a rolled up or folded state at the outside of the tunnel 14.

A covering mechanism 3 may be provided in the tunnel 14 or outside of the tunnel 14. The function of covering mechanism 3 is to pull the sterile cover 2 through the tunnel 14, thereby unrolling or unfolding the sterile cover. The unrolled or unfolded sterile cover 2' is shown in FIG. 2 in the tunnel 14. The unfolded sterile cover 2' in the tunnel may be separated by a perforation 4 from other sterile covers 2 folded outside the tunnel 14. The sterile cover 2, 2' alleviates or avoids the problem of contamination of the bore or imaging device.

Figure 3:
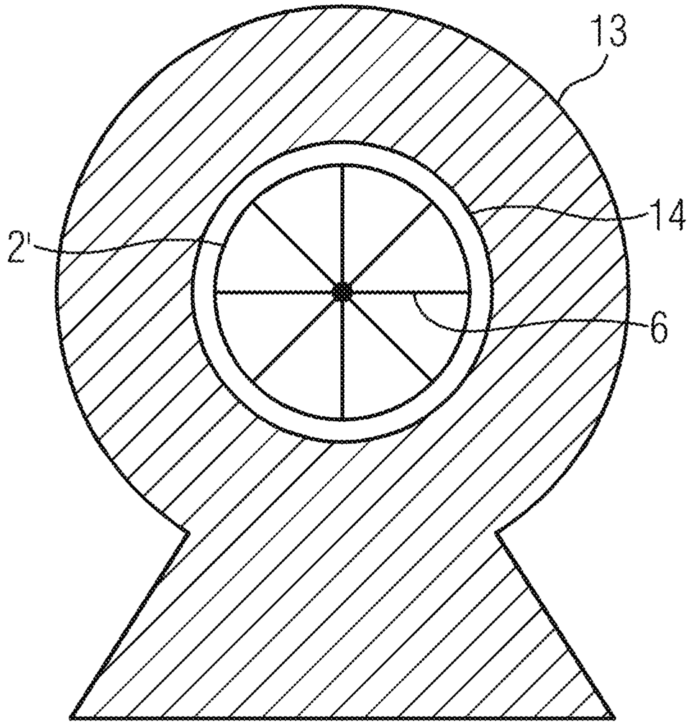
FIG. 3 depicts a cross-sectional view of an example of a magnetic unit of an MRT-device with a sterile cover and a covering mechanism.

In the following, some embodiments of draping the bore of the device with a sterile material are described. According to a first embodiment, the sterile cover 2 is formed like a tube. The sterile cover 2 may be folded in the shape of a ring 5 and positioned at the entrance of tunnel 14. The covering mechanism 3 for unrolling or unfolding the sterile cover 2 may include an umbrella device 6 as shown in the cross-sectional view of the magnet unit 13 in FIG. 3. The draping of the tunnel 14 is performed before the patient 15 is pushed into tunnel 14. The tube shaped sterile cover 2' shall be spread in tunnel 14. For this purpose, the umbrella device 6 may be introduced into the cover tube in order to spread it in tunnel 14. In a first variation, the umbrella device has fixed arms which spread the cover 2' towards the tunnel wall. According to another variation of the umbrella device 6, its arms are movable and are spread within the sterile cover 2' in tunnel 14, thereby pressing the sterile cover 2' towards the inner wall of the tunnel 14.

The plastic foil or paper of the sterile cover 2, 2' may have glue or other sticky material at a surface of the cover to hold the cover against the inner wall of the tunnel. Alternatively, there may be sticky material on the inner wall of the tunnel to detachable fix the cover to the outside of the bore. Furthermore, there may be sticky material on the outside of the covering, to stick a part of the covering to the outside of the bore in such a way that the bore itself is covered.

According to another embodiment, the sterile cover is rolled onto a stick or roll. This stick may be rolled against the bore by the covering mechanism 3 in a circumferential direction. Thereby, the sterile cover 2 is unrolled and released at the inner wall of that bore or tunnel 14. This cover may also have sticky material on its surface to hold it to the bore as described above. During unrolling the rotation axis of the stick is kept in parallel with the center axis 7 of the bore.

In another embodiment, the imaging device, (e.g., the MRT-device 11), is dedicated to intervention. In this case, a storage device or system may be associated with the bore of the imaging device on one or both sides. This storage device or system (one realization is the ring 5 in FIG. 2) releases the plastic or paper cover 2 that may be pulled through to the other side of tunnel 14 and attached to the scanner.

All the above embodiments allow for protecting the inside of the scanner so that accidental or minor contact of interventional equipment with the bore does not break the sterile field.

Figure 4:
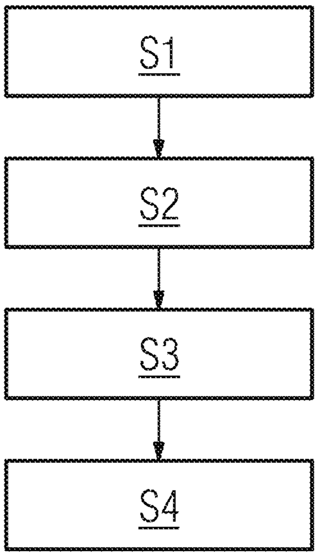
FIG. 4 depicts a schematic block diagram showing an embodiment of the method.

One embodiment of the method is now described in connection with FIG. 4. In act S1, the sterile cover is provided at the outside of the bore 14 of the imaging device 11. The sterile cover 2, 2' may be provided in a folded or rolled state, or in a unfolded or unrolled state.

In act S2, the sterile cover 2, 2' is pulled into the bore. If necessary, the sterile cover 2, 2' is unfolded or unrolled thereby. This act of pulling may be performed by the covering mechanism 3. The covering mechanism may include a linear transport system in parallel to the center axis 7 of the bore and a grabbing device for grabbing the sterile cover 2, 2'.

In a further optional act S3, the sterile cover 2, 2' is pressed against the inner wall of the bore 14. This pressing may be performed by the covering mechanism, 2. For instance, the covering mechanism includes the umbrella device or the stick to be rolled along the inner wall in the circumferential direction as described above.

In a further optional act S4, the sterile cover 2, 2' is stuck or tacked to the inner wall of the bore 14. A suitable glue may be used for this purpose. Alternatively, if the cover may be used multiple times, wherein the cover may be disinfected after each use, a Velcro® fastener may be used for tacking the cover to the inner wall of the bore. Alternatively, other fasteners may be used.

Although the disclosure has been illustrated and described in more detail by the embodiments, the disclosure is not limited by the disclosed examples and other variations may be derived therefrom by those skilled in the art without departing from the scope of protection of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A device for imaging at least a part of a patient, the device comprising:

a detection apparatus comprising a tunnel configured to receive the patient for imaging purposes;

a sterile cover configured to be initially rolled up or folded outside of the tunnel; and a covering mechanism configured to unroll or unfold the sterile cover and drape the sterile cover in the tunnel, such that an inner wall of the tunnel is at least partially covered by the sterile cover, wherein the covering mechanism comprises an umbrella device configured to unfold the sterile cover and press the sterile cover to the inner wall of the tunnel when the umbrella device is pushed through the sterile cover in the tunnel such that the sterile cover is positioned between the inner wall of the tunnel and the umbrella device, and wherein the umbrella device of the covering mechanism is configured to be removed from the tunnel after the sterile cover is pressed to the inner wall of the tunnel and before the patient is moved into the tunnel.

2. The device of claim 1, wherein the sterile cover has a cylindrical shape with a diameter of an order of the tunnel.

3. The device of claim 2, wherein the sterile cover is one cover of a series of covers each separated from another cover of the series of covers by a respective perforation.

4. The device of claim 1, wherein the detection apparatus is based on magnetic resonance (MRT) technology or computed tomography (CT) technology.

5. The device of claim 1, further comprising:
a table configured to transport the patient into the tunnel, wherein the table is configured to be moved into the tunnel covered by the sterile cover after removal of the umbrella device from the tunnel without damaging the sterile cover.

6. The device of claim 1, wherein the sterile cover, the inner wall of the tunnel, or both the sterile cover and the inner wall of the tunnel comprise a sticky material configured to fix the sterile cover at the inner wall of the tunnel via the umbrella device pressing the sterile cover to the inner wall.

7. The device of claim 1, wherein the sterile cover comprises paper or a plastic film.

8. A system configured to perform an image guided intervention, the system comprising:
an intervention device; and
a device for imaging at least a part of a patient, wherein the device comprises:
a detection apparatus comprising a tunnel configured to receive the patient for imaging purposes;
a sterile cover configured to be initially rolled up or folded outside of the tunnel; and
a covering mechanism configured to unroll or unfold the sterile cover and drape the sterile cover in the tunnel, such that an inner wall of the tunnel is at least partially covered by the sterile cover,
wherein the covering mechanism comprises an umbrella device configured to unfold the sterile cover and press the sterile cover to the inner wall of the tunnel when the umbrella device is pushed through the sterile cover in the tunnel such that the sterile cover is positioned between the inner wall of the tunnel and the umbrella device, and
wherein the umbrella device of the covering mechanism is configured to be removed from the tunnel after the sterile cover is pressed to the inner wall of the tunnel and before the patient is moved into the tunnel.

* * * * *